United States Patent
MacArthur

(10) Patent No.: US 6,783,550 B2
(45) Date of Patent: *Aug. 31, 2004

(54) PROSTHESIS AND METHODS FOR UNICOMPARTMENTAL AND TOTAL KNEE ARTHROPLASTY

(76) Inventor: A. Creig MacArthur, 1500 N. 300 West, Suite 212, Provo, UT (US) 84604

(*) Notice: Subject to any disclaimer, the term of this patent is extended or adjusted under 35 U.S.C. 154(b) by 0 days.

This patent is subject to a terminal disclaimer.

(21) Appl. No.: 10/060,430

(22) Filed: Jan. 29, 2002

(65) Prior Publication Data

US 2002/0099446 A1 Jul. 25, 2002

Related U.S. Application Data

(63) Continuation of application No. 09/506,821, filed on Feb. 18, 2000, now Pat. No. 6,342,075.

(51) Int. Cl.[7] .................................................. A61F 2/38
(52) U.S. Cl. ................................ 623/20.14; 623/18.11; 623/19.11
(58) Field of Search ........................... 623/20.15, 20.14, 623/20.11, 20.23, 20.27, 20.29, 20.31, 18.11, 19.11

(56) References Cited

U.S. PATENT DOCUMENTS

| | | | | |
|---|---|---|---|---|
| 5,263,987 A | * | 11/1993 | Shah ....................... 623/18.11 |
| 5,282,868 A | * | 2/1994 | Bahler ..................... 623/20.29 |
| 5,871,541 A | * | 2/1999 | Gerber .................... 623/20.29 |
| 5,871,546 A | * | 2/1999 | Colleran et al. .......... 623/20.28 |
| 5,879,389 A | * | 3/1999 | Koshino ................... 623/20.11 |
| 6,051,751 A | * | 4/2000 | Sioshansi et al. ........... 128/898 |
| 6,171,340 B1 | * | 1/2001 | McDowell ................ 623/18.11 |
| 6,342,075 B1 | * | 1/2002 | MacArthur ............... 623/20.14 |

OTHER PUBLICATIONS

Biomet, Inc., Repicci II, Unicondylar Program, *Minimally Invasive Surgical Technique*, 1998.

* cited by examiner

Primary Examiner—Pedro Philogene
(74) Attorney, Agent, or Firm—Holme Roberts & Owen LLP

(57) ABSTRACT

A knee joint prosthesis, comprising at least one femoral component and at least one tibial component. The femoral component having a first portion adapted for fixable attachment to a distal end of a femur and a second portion formed with a bearing surface. The femoral component is sized so as to permit attachment to the femur of a patient without severing at least one the cruciate ligaments. The tibial component has a first surface that is adapted to cooperate with a patient's tibia, while a second surface of the tibial component is adapted to cooperate with the femoral component. The tibial component is sized so as to permit attachment to the patient's tibia without severing at least one of the cruciate ligaments.

39 Claims, 9 Drawing Sheets

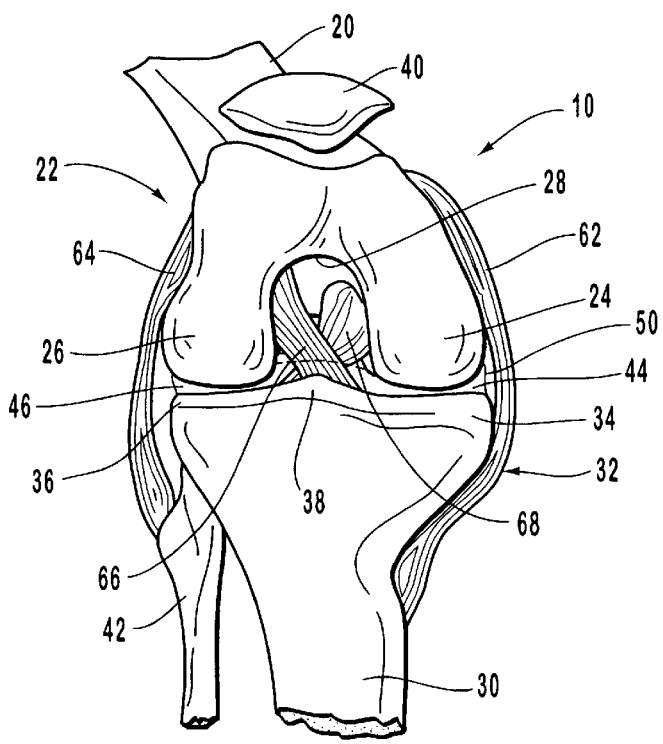
FIG. 1
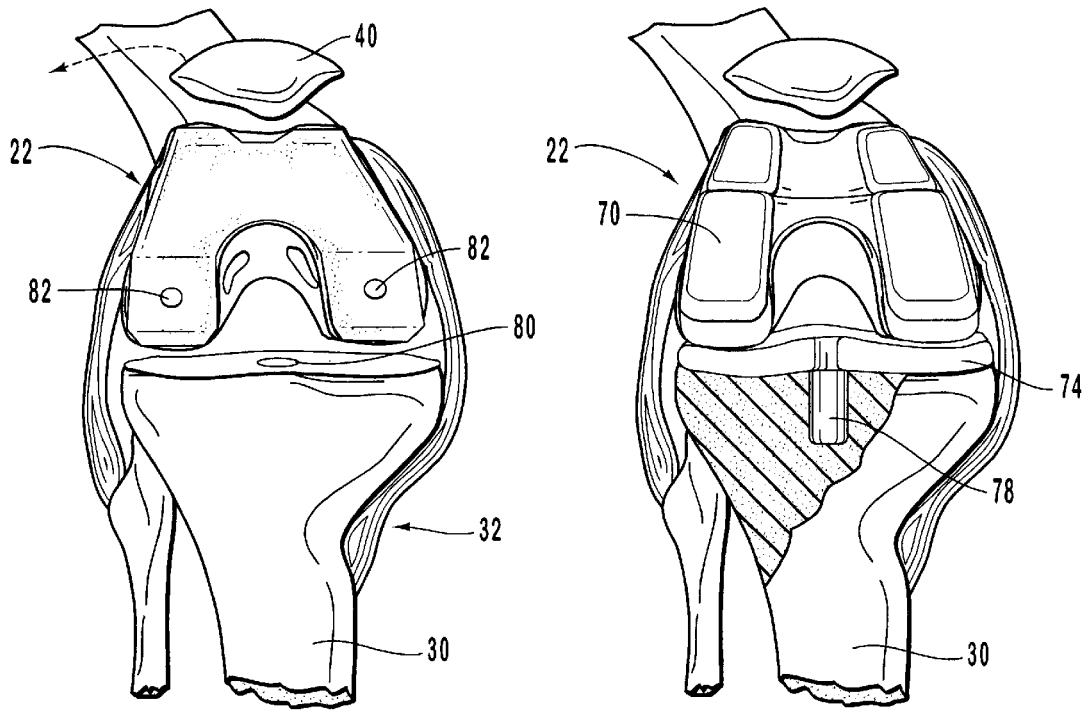
FIG. 2
(PRIOR ART)
FIG. 3
(PRIOR ART)

PROSTHESIS AND METHODS FOR UNICOMPARTMENTAL AND TOTAL KNEE ARTHROPLASTY

CROSS-REFERENCE TO RELATED APPLICATIONS

This is a continuation patent application of, and claims priority to, U.S. patent application Ser. No. 09/506,821, filed Feb. 18, 2000 now U.S. Pat. No. 6,342,075 entitled "Methods and Prosthesis for Total Knee Arthroplasty," the disclosure of which is incorporated herein by this reference.

BACKGROUND OF THE INVENTION

1. The Field of the Invention

The present invention relates to prosthetic structures and corresponding surgical methods used to relieve pain caused by disorders of the knee joint. More particularly, the invention relates to prostheses and methods for total knee arthroplasty.

2. The Relevant Technology

The knee is the largest and one of the most complicated joints of the human body. The human knee joint serves an essential function to allow individuals to lead a normal life, while performing its function, in many ways, much better than any device heretofore designed by human engineers. For example, the knee should be able to move from 0° in the straight position to more than 90°, while being completely stable in every other direction.

The bones of the knee joint, when functioning properly, move together with very little friction. To function properly, a healthy knee joint requires an intact layer of hyaline cartilage, the material that makes up the articular cartilage on opposing surfaces of the joint. In addition, the bones of the joint must be in proper alignment and the synovial membranes must produce sufficient amounts of lubricating (synovial) fluid. Furthermore, the surrounding ligaments and tendons must prevent the bones from being placed in abnormal positions.

FIG. 1 is an anterior (that is, taken from the front of the body) cross-sectional view of a human knee 10. The knee 10 consists of three bones; a femur 20, a tibia 30, and a patella 40. Each of these bones is covered with articular cartilage, which has a smooth glistening surface. Located at the distal end of femur 20 are the femoral condyles 22 having a medial condyle 24 and a lateral condyle 26 separated by an intercondylar fossa or notch 28. Formation of intercondylar notch 28 is such that patella 40 articulates therethrough during extension and flexion of knee 10.

Tibia 30 supports most of the weight transmitted between femur 20 and the foot (not shown), while a small portion of the weight is carried by a fibula 42 located substantially parallel to tibia 30. As such, tibia 30 has a tibial plateau 32 with a medial plateau 34 and a lateral plateau 36 substantially aligned to cooperate with medial condyle 24 and lateral condyle 26 of femur 20. Medial plateau 34 and lateral plateau 36 of tibia 30 are separated by an intercondylar area formed with an elevated portion or an intercondylar eminence 38. Intercondylar eminence 38 locates within intercondylar notch 28 to maintain structural support between femur 20 and tibia 30. Additionally, intercondylar notch 28 separates the spaces of a medial compartment 44 and a lateral compartment 46 formed between the respective medial and lateral plateaus 34, 36.

Located within each medial and lateral compartment 44 and 46 are the menisci 50, shown by the dotted line. Menisci 50 consists of two crescentic lamellae formed to distribute surface stresses between femur 20 and tibia 30. As such, the upper surfaces of the menisci 50 are smooth and concave to accommodate femoral condyles 24 and 26, while the lower surfaces are smooth and flat to cooperate with tibial plateaus 34 and 36.

Surrounding and stabilizing the dynamic structure of knee 10 are a number of varyingly sized ligaments. Particularly, four main ligaments maintain the stability and flexibility of knee 10: a medial collateral ligament 62, a lateral collateral ligament 64, an anterior cruciate ligament 66 and a posterior cruciate ligament 68. Medial collateral ligament 62 and lateral collateral ligament 64 limit side-to-side motion. Medial collateral ligament 62 extends from medial condyle 24 or portions of femur 20 to medial plateau 34 of tibia 30. Similarly, lateral collateral ligament 64 extends from lateral plateau 36 or portions of femur 20 to fibula 42. Anterior cruciate ligament 66 and posterior cruciate ligament 68, so named because they cross in the middle of knee 10, are rope-like ligaments formed from interwoven and overlapping fibers. Anterior cruciate ligament 66 and posterior cruciate ligament 68, extend from the anterior to the posterior of knee 10 and prevent femur 20 and tibia 30 from sliding forward and backward while permitting a wide range of rotational movement.

While the knee generally serves its purpose very well, various disorders of the knee cause a great deal of pain and loss of mobility and function to those who are affected with such disorder. Some knee disorders are congenital; that is, they are present at birth. Other disorders of the knee are brought on by bacterial infections that may occur at any age. Yet still other disorders result from normal "wear and tear" of the knee joint, whether such "wear and tear" arises from age or injury. Perhaps the most wide spread disorder of the knee is arthritis. The term "arthritis" is generally used as a common name for the effects of several degenerative knee disorders, such as by way of example traumatic arthritis, infectious arthritis, osteoarthritis, and rheumatoid arthritis.

Of various types of arthritis, osteoarthritis is perhaps the most common. Osteoarthritis is a degenerative "wear and tear" process that affects substantial numbers of people. The final result of unchecked osteoarthritis is damaged articular cartilage, and subchondral bone which in many cases causes extreme pain as the damaged surfaces are rubbed together during joint movement. Osteoarthritis may also be caused by angular deformity or old fractures. Systemic arthritis such as rheumatoid arthritis or gout affects the synovium (the membrane tissue in the knee that normally lubricates the knee), becomes pathologic and one or more surfaces of the joint are destroyed.

Osteoarthritis may also involve the development of abnormal bone subjacent to the joint surface, known as subchrondral lesions. These subchrondral lesions may take the form of a cyst or sclerosis. Due to the decreased stability of the knee through the generation of cysts and sclerosis and decreased joint space, marginal spurs develop in an attempt to stabilize the joint. Unfortunately, the spurs also cause severe pain, stiffness decreased range of motion, loss of stability, and loss of function.

Generally, osteoarthritis affects people past the age of 60 years without providing any easily recognizable single cause. However, osteoarthritis may develop in younger people due to congenital disease. Furthermore, traumatic injury may cause development of an osteoarthritis condition, such as from various sporting activities.

In the prior art, several methods have been used for alleviating the pain and improving the function of a knee joint affected with a degenerative disorder such as osteoarthritis. One of the most common procedures used in treatment of knee disorders is know as "arthroplasty" and entails the implantation of an artificial joint component into the knee. Arthroplasty has been one of the major areas of advancement in knee surgery during the past quarter century. Knee arthroplasty can take the form of unicompartmental arthroplasty or total knee arthroplasty.

Unicompartmental arthroplasty involves replacement of one of the two compartments of the knee joint. For example, this procedure is used where either of the medial or lateral compartments is damaged, while the remaining compartment and intercondylar notch are otherwise normal. In such a case, it is beneficial to replace the damaged areas of the femoral condyle and tibial plateau with an artificial prosthesis that will work in conjunction with the natural portions of the knee.

The most common arthroplasty procedure used to alleviate pain and restore knee function is total knee arthroplasty, also called total knee replacement. While many different styles of total knee replacement prostheses have been implanted in patients, they generally resemble the prosthetic illustrated in FIG. 3.

Conventional total knee replacement involves a complete resurfacing of both tibial plateaus 34, 46 and femoral condyle 24, 26 as suggested in FIGS. 2 and 3. The conventional surgical procedure used during total knee replacement involves the insertion of one or all of the following artificial components into the knee; a one piece metallic femoral component 70, a one piece metallic tibial tray component 74 with a polyethylene insert (not shown), and a one piece patellar component (not shown) of polyethylene. Each component 70 and 74 is adapted to cooperate one with another. As commonly used, femoral component 72 and tibial component 74 include one or more stems 78, as shown in FIG. 3, that are used to fixably attach respective components 72 and 74 to their respective bones.

As depicted in FIGS. 2 and 3, the present procedure for total knee replacement is extremely invasive, causing significant damage to the muscles, tendons and ligaments surrounding knee 10. The traditional surgical procedure entails making a large surgical incision over the front of knee 10. Patella 40 is slipped across to the outside of knee 10 to expose the joint between femur 20 and tibia 30, as shown by the dotted line. Any excess bone, such as subchrondral lesions, formed on either femoral condyles 24 and 26, or tibial plateaus 34 and 36 is removed and tight soft tissue carefully released so that knee 10 returns to its normal shape without becoming too loose. Following removal of excess bone, the worn bone surfaces are cut away, while anterior cruciate ligament 66 and posterior cruciate ligament 68 are removed. The resultant bone surfaces are sized and holes 80 and 82 are drilled into femoral condyle 22 and tibial plateau 24. Specifically, as shown in FIG. 2, hole 80 is drilled into the medullary canal (not shown) to accommodate tibial tray component 34.

During drilling of holes 80 and 82 high tolerances must be maintained, since misalignment of femoral component 70 and tibial tray component 74 results in a misaligned knee joint, thereby eliminating the beneficial effects of the surgical procedure. Once prepared, exact replicas of the real artificial components are placed in position with holes 80 and 82 to allow testing of joint stability and dynamic motion. Upon completion of testing, the replicas are removed and the prosthetic components are fixed in position.

The most commonly accepted method of fixing femoral and tibial tray components 70 and 74 to femur 20 and tibia 30 is through the use of a cement, such as polymethyl methacrylate (PMMA) or porous ingrowth press fit. PMMA is a two-component acrylic cement that has the advantage of accepting a rapid setting time. After mixing the two components of the acrylic cement, holes 80 and 82 are "packed" with unset PMMA. The stems of femoral component 70 are located within holes 82 while stem 78 of tibial component 74 is located within hole 80. Both femoral component 70 and tibial component 74 are maintained in place until PMMA sets. Once the PMMA has set, the insert (not shown) is located between tibial tray component 74 and femoral component 70 and the necessary positioning of patellar component 72 is performed.

Due to the various sizes and dimensions of knee 10, each component 70 and 74 is available in a wide variety of sizes and styles. During the surgical procedure, 10–20 different prosthetic components may be available to a physician. Currently, most of the prosthetic femoral components 70 and tibial tray components 74 are fabricated from alloys containing stainless steel, chromium, cobalt, molybdenum, or titanium. Such materials are inert within the body and maintain good mechanical properties. Tibial tray component 74 is most often made of titanium or stainless steel that is strong and leaves space for the insert. The insert traditionally comprises a plastic material, usually manufactured from an ultra-high molecular weight polyethylene (UHMWP), because it is chemically similar to ordinary polyethylene but much harder and very smooth. Unfortunately, there is a significant manufacturing cost with these prostheses.

While the conventional total knee prosthesis procedure has been popularly accepted, major risks and drawbacks accompany its use. First, the required long incision either anteriorly or posteriorly disrupts the extensor mechanism of the knee, such as the quadricep muscles, thus prolonging rehabilitation.

Second, traditional total knee replacement requires the removal of a large amount of bone from femur 20 and tibia 30, while necessitating insertion of a large amount of foreign material. Insertion of foreign material creates a significant "dead space" in the knee where an individual has no feeling, while increasing the risk of infection.

Third, the total knee replacement procedure eliminates the stability provided by both anterior and posterior cruciate ligaments 66 and 68 of the knee 10. During current surgical procedures, commonly both anterior and posterior cruciate ligaments 66 and 68 are removed. Therefore, only the combination of medial and lateral collateral ligaments 62 and 64 with the configuration of the prosthesis maintains a stability of knee 10.

Fourth, since tibial tray component 74 covers both the medial and lateral portions of tibial plateau 32, a tilting motion occurs during normal motion of knee 10. The tilting motion causes a predisposition to loosening of the bond between tibial tray component 74 and tibia 30. Furthermore, the abnormal motion of medial and lateral portions of tibial plateau 32 result in abnormal dynamic knee motion, thereby disrupting the normal "screw mechanism" of the knee, i.e. the external rotation of tibia 30 relative to femur 20 in the final 20° motion of the knee extension. As such, an abnormal gait pattern can occur resulting in a predisposition for serious complications (such as loosening, infection, osteolysis, bone loss, etc).

Fifth, as mentioned earlier, the most common method of fixing the components of a total knee prosthesis is by way of PMMA. PMMA cement is prepared by mixing two components together which harden into a solid mass by way of a chemical process. One of the two components is a fine granular powder of prepolymerized polymethyl methacrylate and the other component is a liquid monomer. One constituent of the liquid monomer is N, N-Dimethyl-Para-Toluidine (DMPT), a toxic material. Other monomer ingredients also exhibit adverse effects on humans. Thus, the introduction of the mixed, but yet unset, PMMA, cement mixture into holes 80 and 82, presents the potential of introducing a significant amount of toxic material into the blood stream, especially when locating the stems of the prosthesis into the medullary canal. Various reactions can occur to PMMA cement, such as hypotension and even circulatory system collapse.

Aside from the immediate hazards that attend the use of PMMA cement, concern has also been expressed that there may be long term toxicity, hypersensitivity, and carcinogenicity resulting from the materials that make up prior total knee prosthesis, including cobalt, chrome, titanium, and polyethylene. In view of the uncertainty of the effects of long-term use of these materials within the human body, it has been considered advisable to reduce the contact between these materials and the body as much as possible.

Finally, in any surgical procedure there is the potential that infection may occur due to entry of microorganisms into the surgical wound. Devastating infections are particularly difficult to prevent in total knee replacement procedures due to the extensive invasion of the body that is required. Special surgical techniques have been developed which reduce the risk of infection to the patient; unfortunately, these surgical techniques require far greater care than other types of surgical procedures, and in some cases are extremely cumbersome.

BRIEF SUMMARY OF THE INVENTION

It is a primary object of the invention to provide structures and methods for reducing pain and instability, while improving function to damaged or diseased knees.

A particular object of the present invention is to provide structures and methods for augmenting portions of the femur and the tibia, in order to reduce or eliminate pain, improve range of motion, and enhance function of the joint.

Another object of the invention is to provide structures and methods that minimize the quantity of bone mass required to be removed for total or unicompartmental knee arthroplasty.

Another object of the invention is to provide structures and methods for repairing a damaged or diseased knee joint which are significantly less invasive than prior art methods of knee arthroplasty.

Yet another object of the invention is to provide structures and methods for reducing pain and increasing function of a diseased knee joint in which foreign material presented to the body tissues and fluids is reduced to a minimum.

Still yet another object of the invention is to provide structures and methods for repairing damaged or diseased portions of a knee that minimize the possibility and consequences of infection entering the wound resulting from knee arthroplasty.

Another object of the invention is to provide knee prosthetic structures that are simpler to manufacture and cost less than those prostheses available at present.

Yet another object of the invention is to provide structures and methods that reduce the wound size, surgical procedure time, and length of accompanying in hospital stay.

Still another object of the invention is to provide structures and methods for reducing pain and increasing function of a knee that results in a less painful rehabilitation while achieving increased range of motion with similar stability as that of a healthy knee joint.

Still yet another object of the present invention is to preserve the anterior cruciate ligament and the posterior cruciate ligament to preserve a more normal gait pattern.

Yet another object of the present invention is to preserve the normal radius of curvature of the knee, thus preserving the screw home mechanism of the knee.

Another object of the present invention is to provide for more efficient boundary lubrication of the prosthetic components, thus reducing friction and associated problems.

To achieve the forgoing objects and in accordance with the invention as embodied and broadly described herein, a knee joint prosthesis is disclosed. The knee joint prosthesis includes one or more femoral components and one or more tibial components. The femoral components are adapted for attachment to a femur of a patient while retaining the cruciate ligaments. Each femoral component has a generally spheroidal weight-bearing surface and includes a stem that is used to fixably attach the femoral component to the patient's femur. The tibial component has a first surface configured to aid in attachment of the tibial component to a tibia while a second surface is adapted to cooperate with the bearing surfaces of the femoral components.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the present invention are obtained, a more particular description of the invention will be rendered by reference to specific embodiments thereof that are illustrated in the appended drawings. Understanding that these drawings depict only typical embodiments of the invention and are therefore not to be considered limiting of its scope, the invention will be described and explained with additional specificity and detail through the use of the accompanying drawings in which:

FIG. 1 is a cross-sectional view showing the major structures of the human knee.

FIG. 2 is a partial cross-sectional view of a human knee in which the human knee has been prepared for total knee replacement, using a prior art prosthesis.

FIG. 3 is a partial cross-sectional view of a human knee in which a total knee replacement common in the prior art has been implanted to replace the natural knee.

Figure 4:
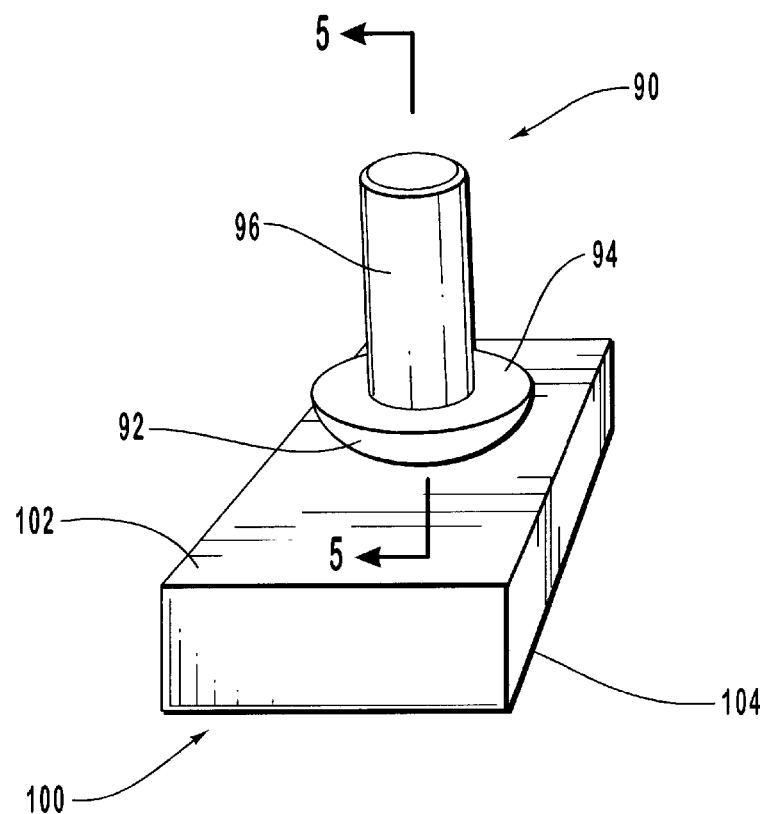
FIG. 4 is a perspective view of the femoral and tibial components of a presently preferred embodiment of the present invention.

DETAILED DESCRIPTION OF THE PREFERRED EMBODIMENTS (a) Introduction

The present invention includes various prosthetic components and methods for surgically implanting such prosthetic components in a human knee to reduce pain, improve motion, and enhance function of a diseased or damaged knee joint. Each prosthetic component is sized and shaped to allow the method for implantation to minimize the wound size and invasiveness of the surgical procedure, thereby reducing cost, hospital stay, rehabilitation time, and pain.

Generally, a patient postpones obtaining medical treatment until the pain due to a knee disorder is severe. By this time, various parts of the knee are generally involved in causing the patient's pain and a corresponding reduction of knee motion and function, such as the femoral condyle, the tibial plateau, the patella, and the menisci. It is frequently necessary to take corrective action by treating all of the above knee elements. The present invention includes both femoral and tibial prosthetic components adapted for replacement of damaged tissue and bone, whether for total or unicompartmental knee joint replacement. Generally, the components will be used in cooperation with each other, although it should be understood that single components might be utilized to obtain the desired result.

The following description is divided into several parts in order to improve clarity of the description and to assist the reader in understanding the concepts involved. First a description of various causes of pain in the knee are given so that is will be clear how the present invention helps to reduce or eliminate such pain and thus improve knee joint motion and function. Upon this foundation, a detailed description of the presently preferred embodiments of the present invention is provided together with a brief explanation of protocols and procedures in accordance with the invention.

(b) Localization of Knee Pain

As described previously, there are various reasons for pain within knee joints. Such pain can result from sporting injuries or accidents, hereditary joint malformation or disease, contracted diseases, or simply "wear and tear." Each particular infirmity can affect the knee joint in a different manner. For example, malformation of joint surfaces can cause joint instability, deterioration of internal bone structures resulting in the disintegration of bone mass, or elimination of the menisci.

Generally, pain occurs when the bony surfaces of the femur and tibia come into contact. Specifically, pain can result when the bony medial and lateral condyles of the femur grind against the medial and lateral surfaces of the tibial plateau, whether as a result of deterioration of the articular cartilage between the surfaces of the femur and the tibia, or due to some other reason which will be appreciated by one skilled in the art. Due to the structure of the skeleton, constant force is applied to the femoral and tibial surfaces during normal physical activity, such as walking. In the case where the menisci has disintegrated or thinned, the medial and lateral collateral ligaments and the anterior and posterior cruciate ligaments maintain femoral and tibial surfaces in contact, even when seated, thereby generating pain. Pain can also result from the creation of subchrondral lesions that scrape against either the femoral condyles or tibial plateaus. Although there is considerable debate within the medical profession as to the exact cause of knee pain, it is clear that by separating bone surfaces the pain is substantially reduced or eliminated.

(c) Description of the Components of the Presently Preferred Embodiments of the Present Invention As previously stated, the preferred method for preventing pain to the patient is to remove diseased portions of the femoral and tibial articulating surfaces and implant femoral and tibial components. This procedure causes a separation between the bone surfaces, thereby eliminating knee pain. The present invention effectively creates bone surface separation in a substantially less invasive manner.

Reference will now be made to FIGS. 4–10 to describe the structure of the components of the presently preferred embodiments. In the drawings, like structures are marked with like numerals.

One presently preferred embodiment of the present invention is shown in perspective in FIG. 4. The structure of this embodiment includes two prosthetic components useful in either total or unicompartmental knee replacement of portion of the intercondylar notch and/or and the medial and lateral condylar surfaces of femoral condyles 22 and the tibial plateaus of tibial plateau 32. The structure of FIG. 4 includes at least one femoral component 90 and at least one tibial component 100. It can be appreciated that in some situations a patellar component and/or an insert may also form part of the structure, so long as such components are adapted for use with the methods and apparatus of the present invention. As mentioned previously, the present invention may use both prosthetic components 90 and 100 together or separately to achieve the beneficial effect of total or unicompartmental knee replacement.

Figure 5:
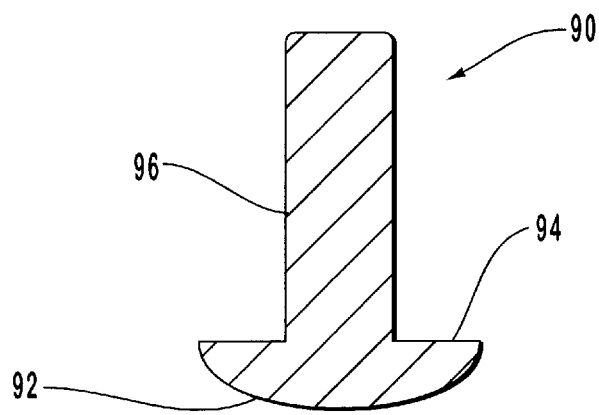
FIG. 5 is a cross-sectional view of a femoral component of the embodiment illustrated in FIG. 4 taken along line 5—5 of FIG. 4.

As depicted, femoral component 90 has a generally T-shaped cross-section, as better seen in FIG. 5, and includes a lower surface portion 92 having a substantially spheroidal shape, and a generally planar superior surface 94 with a fixation post or stem 96 extending therefrom. The term "spheroidal," as used herein, refers to a surface which may either be perfectly spherical, or which departs therefrom, such as being elliptical, or the like. Additionally, spheroidal refers to elongated surfaces having a curved, spherical, or the like profiles. Generally, lower surface portion 92 can take various forms so long as it is capable of cooperating with respective surfaces of tibial components 100. Additionally, lower surface portion 92 acts as a bearing surface through which the weight of the patient is transferred to tibial component 100. Lower surface portion 92 is preferably polished to a mirror-type finish to thereby reduce friction between femoral condyle 22 and tibial plateau 32 and enhances smooth movement of knee 10. Additionally, lower surface portion 92 may be hardened through conventional processing steps to protect the finished surface during use of femoral component 90. As such, lower surface portion 92 is preferably configured from the same material as the rest of femoral component 90, such as but not limited to polyethylene, ceramic, stainless steel, titanium, and the like, or alternatively may be configured from an insert manufactured from a different material than that of the rest of femoral component 90. Furthermore, though it is preferred that lower surface portion 92 be fabricated from substantially the same materials as the rest of femoral component 90, it is contemplated that a friction reducing coating or finish may be applied to lower surface portion 92, such as diamond, and the like, to aid in the movement of the knee joint.

Superior surface 94 is depicted as having a generally planar form, although, various other configurations are also possible, such as curved, spheroidal, angular, or the like, dependent on the particular portion of femoral condyle 22 that is affixed to femur 20. Additionally, superior surface 94 need not be circular in cross-section but may have various other shapes such as, by way of example only, square, triangular, octagonal, hexagonal, oval, trapezoidal, rectangular, or the like.

As referenced previously, femoral component 90 is provided with a stem 96. Stem 96 is depicted as having a generally cylindrical form, although other configurations, shapes and, lengths are possible. As FIGS. 4 and 5 depict, the surface of stem 96 as being generally smooth, although this is not necessary. Stem 96 is adapted to fixably attach to femur 20 and retain femoral component 90 thereto. Stem 96 can, therefore, have various dimensions, sizes, shapes, and cross-sections so long as it is capable of fixably attaching femoral component 90 to femur 20. By way of example and not limitation, such steps include, but are not limited to round, square, oval, triangular, or the like.

Femoral component 90 can have various other configurations, shapes, and dimensions, such as these shown in FIGS. 6A–6G, which shall be described hereinafter. The various configurations can be chosen in light of the size of knee 10, the amount of damage to knee 10, the cooperation between tibial component 100 and femoral component 90, or other reasons that will be appreciated by one skilled in the art.

Femoral component 90 may be advantageously fabricated from various materials, such as metals, ceramics, plastics, or combinations thereof with or without porous ingrowth coatings. In one preferred embodiment, femoral component 90 is fabricated from a stainless steel alloy known in the art as 316L. Stainless steel 316L has the advantage of being easily machined, an economical method of fabrication when dealing in small quantities.

Figure 7A:
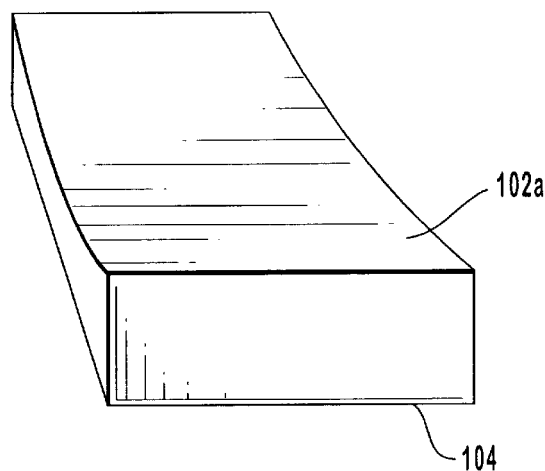
FIGS. 7A–7C are perspective views of alternate configurations of the tibial components in accordance with the present invention.
Figure 7B:
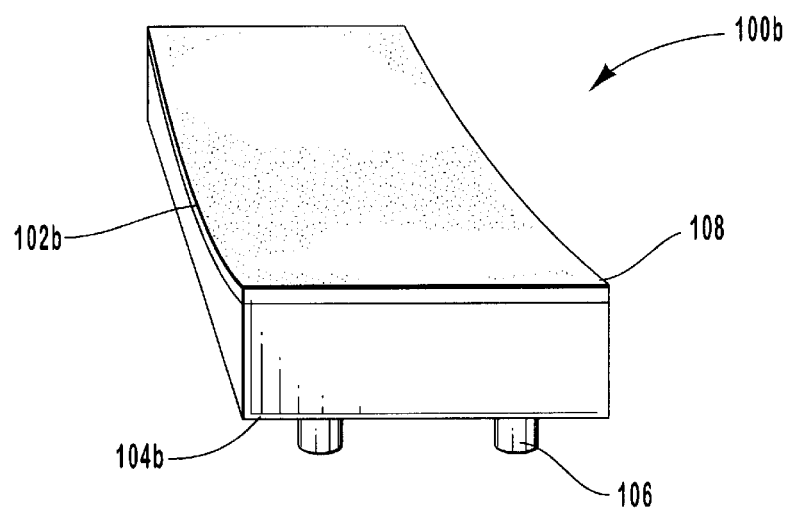
Figure 7C:
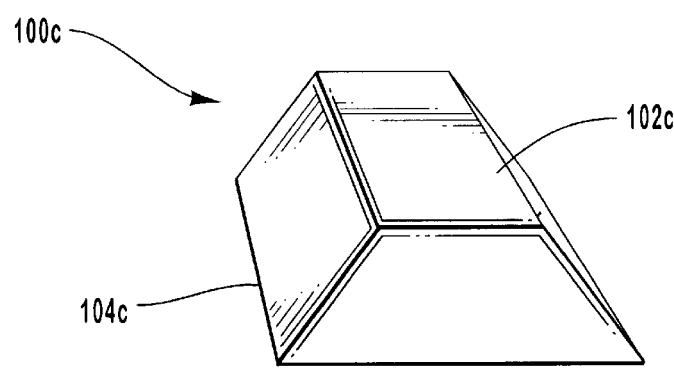

Tibial component 100, as depicted in FIG. 4, has a generally rectangular form having an upper surface 102 and a lower surface 104. The configuration of upper surface 102 is such to cooperate with femoral component 90. As shown, upper surface 102 is generally planar and is preferably polished to a mirror-type finish similar to lower surface portion 92 of femoral component 90. Upper surface 102, may be concave to allow mating with femoral component 90, such as shown in FIGS. 7A and 7B, or may be angularly oriented, or have some other form, such as shown in FIG. 7C. Lower surface 104, as shown in FIG. 4, is also preferably planar and is shaped to cooperate with medial and lateral plateaus 34 and 36 of tibial plateau 32. Although depicted as having a rectangular shape in FIG. 4, lower surface 104 can be concave, convex, planar, angular, or the like, dependent on whether lower surface 104 is inserted within tibial plateau 32, on the surface of medial plateau 34 or lateral plateaus 34, or in some other manner.

Figure 8A:
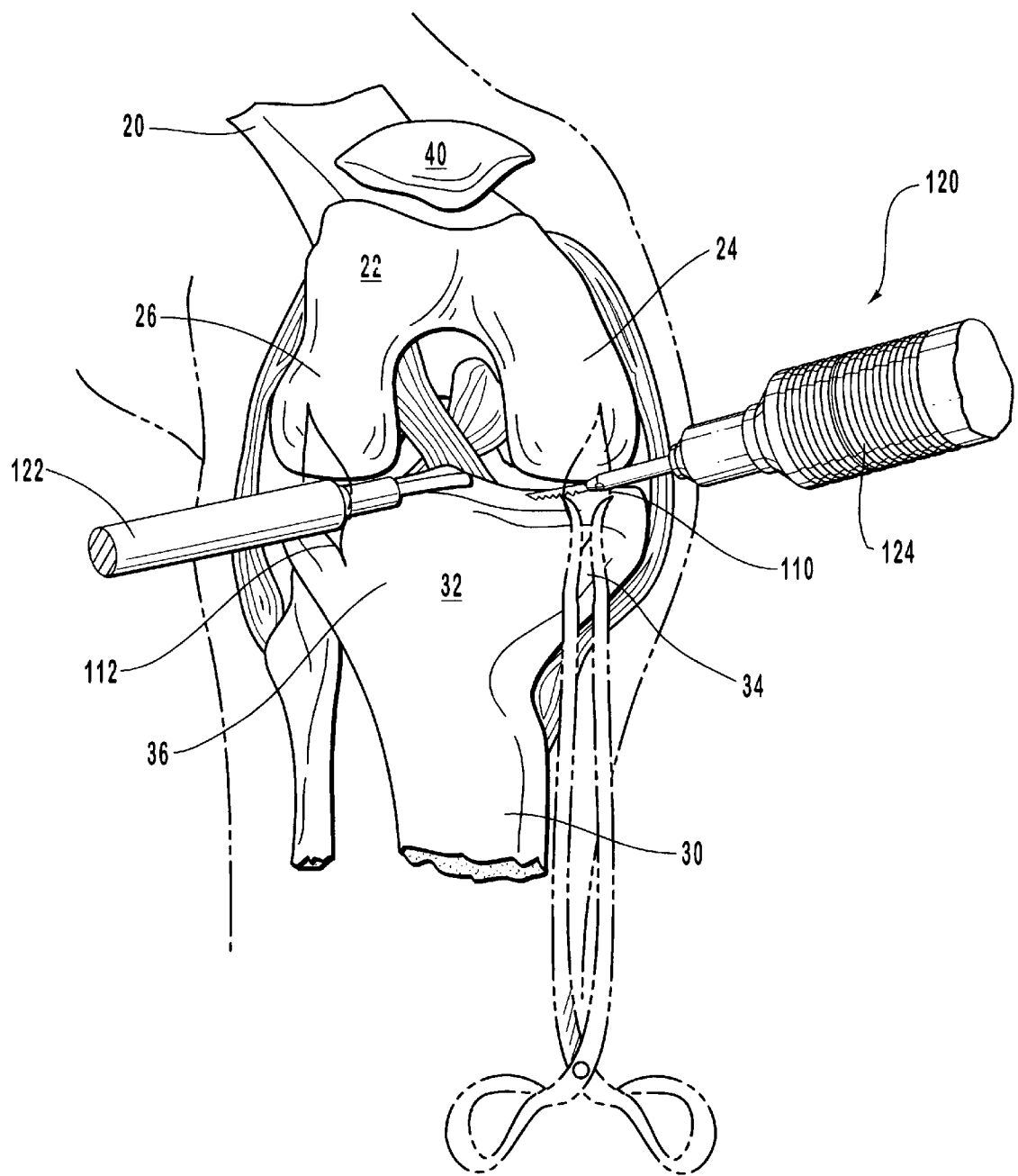
FIG. 8A is a partial cut-away perspective view of the knee joint before removal of portions of the femoral condyle and tibial plateau before implantation of the knee joint prosthesis of the present invention.
Figure 8B:
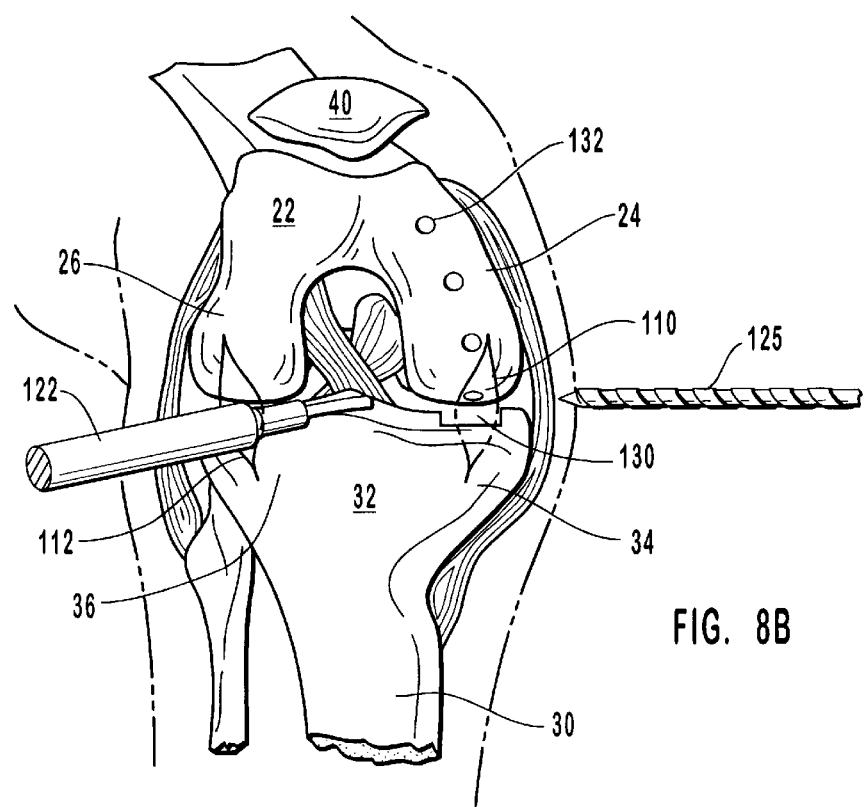
FIG. 8B is a partial cut-away perspective view of the knee joint after removal of portions of the femoral condyle and tibial plateau before implantation of the knee joint prosthesis of the present invention.
Figure 8C:
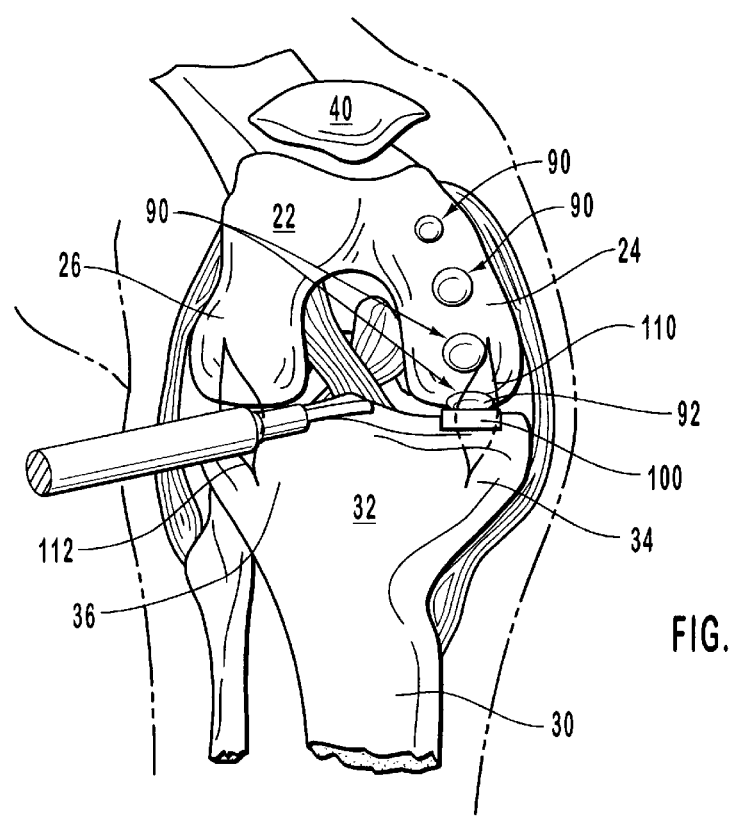
FIG. 8C is a partial cut-away perspective view of the knee joint after implantation of four femoral components and a tibial component of the knee joint prosthesis of the present invention.
Figure 8D:
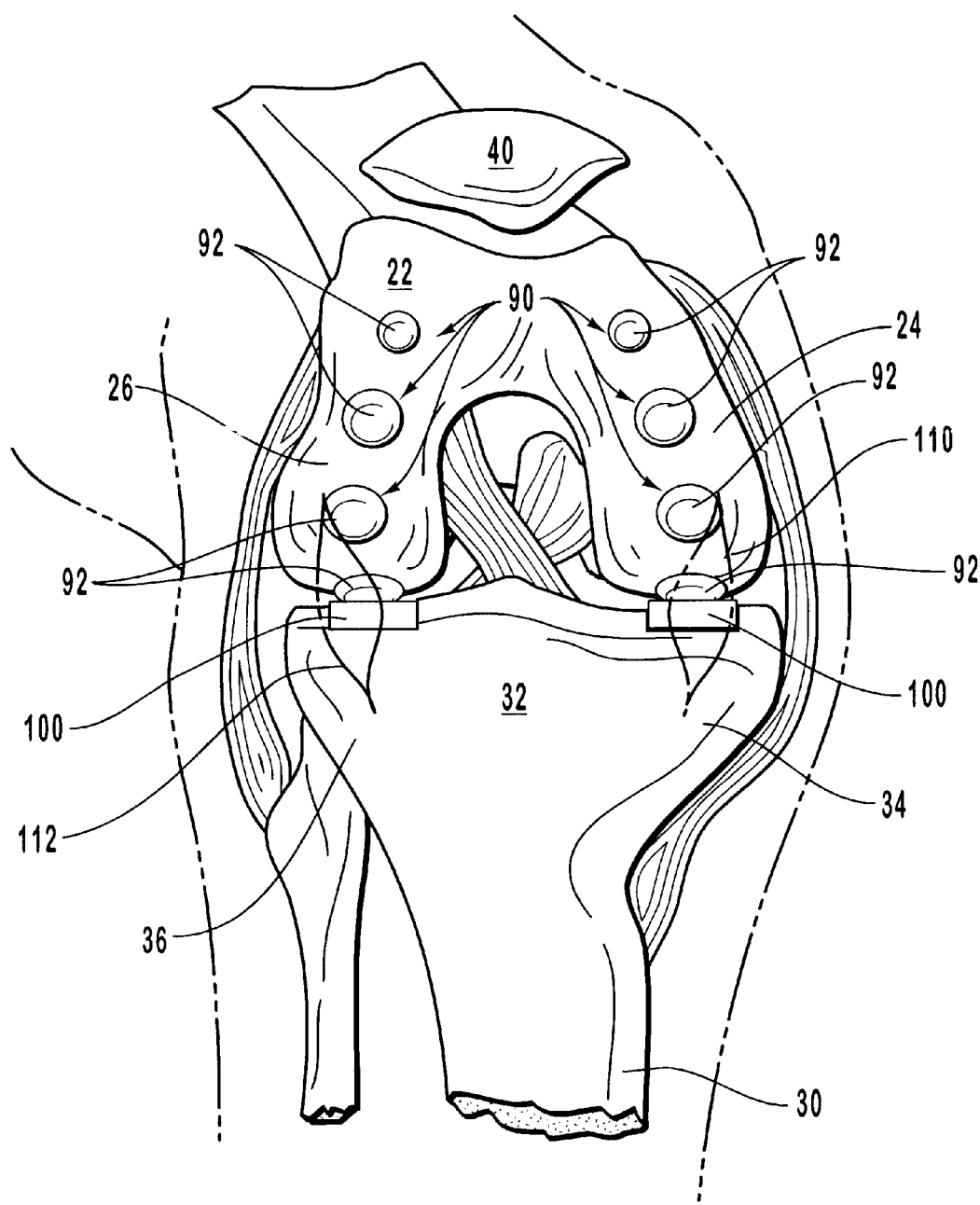
FIGS. 8D is a partial cut-away perspective view of the knee joint with the total knee joint prosthesis of the present invention implanted.
Figure 9:
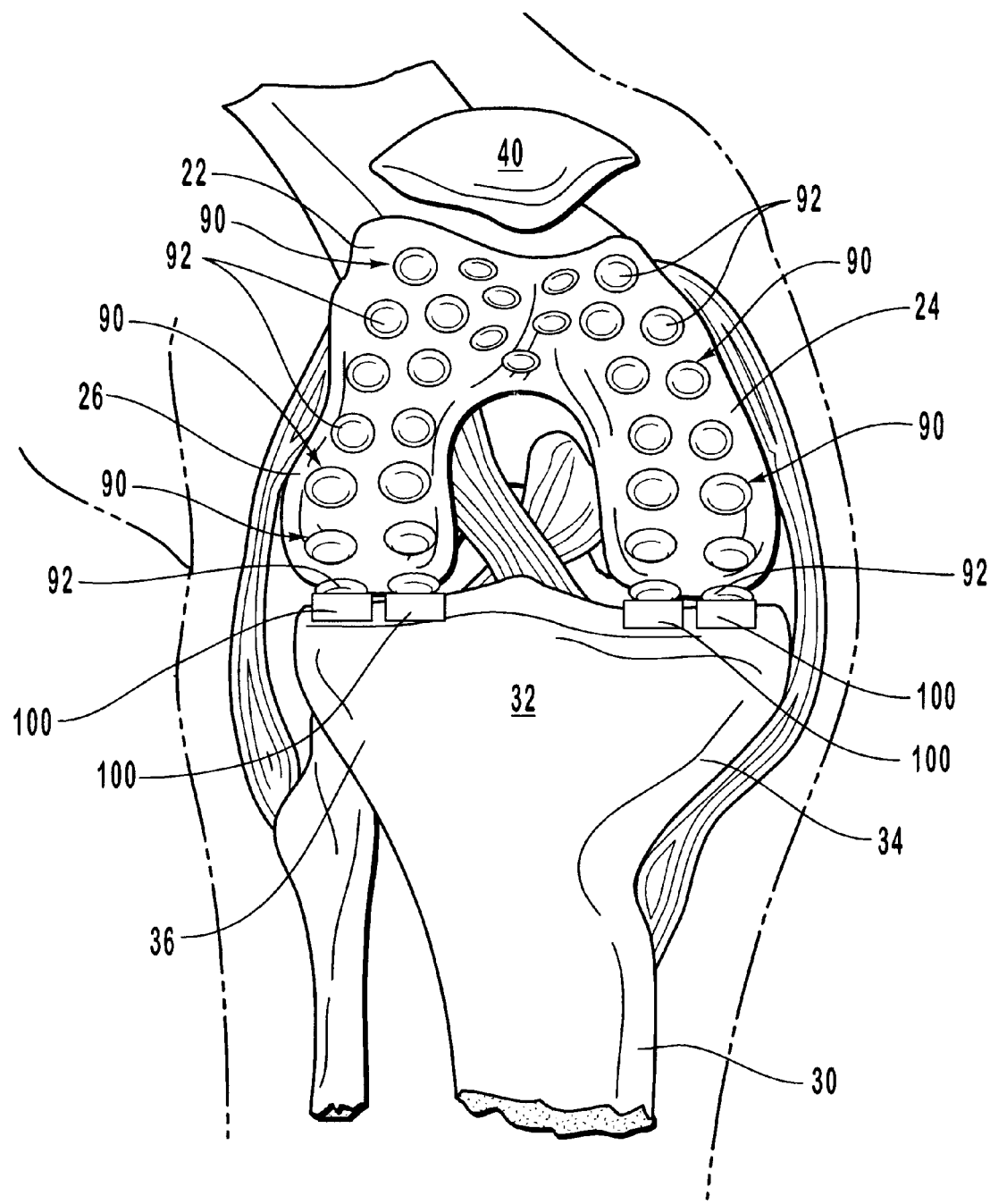
FIG. 9 is a partial cut-away perspective view of a knee joint that includes a alternate form of a total knee joint prosthesis in accordance with the present invention.
Figure 10:
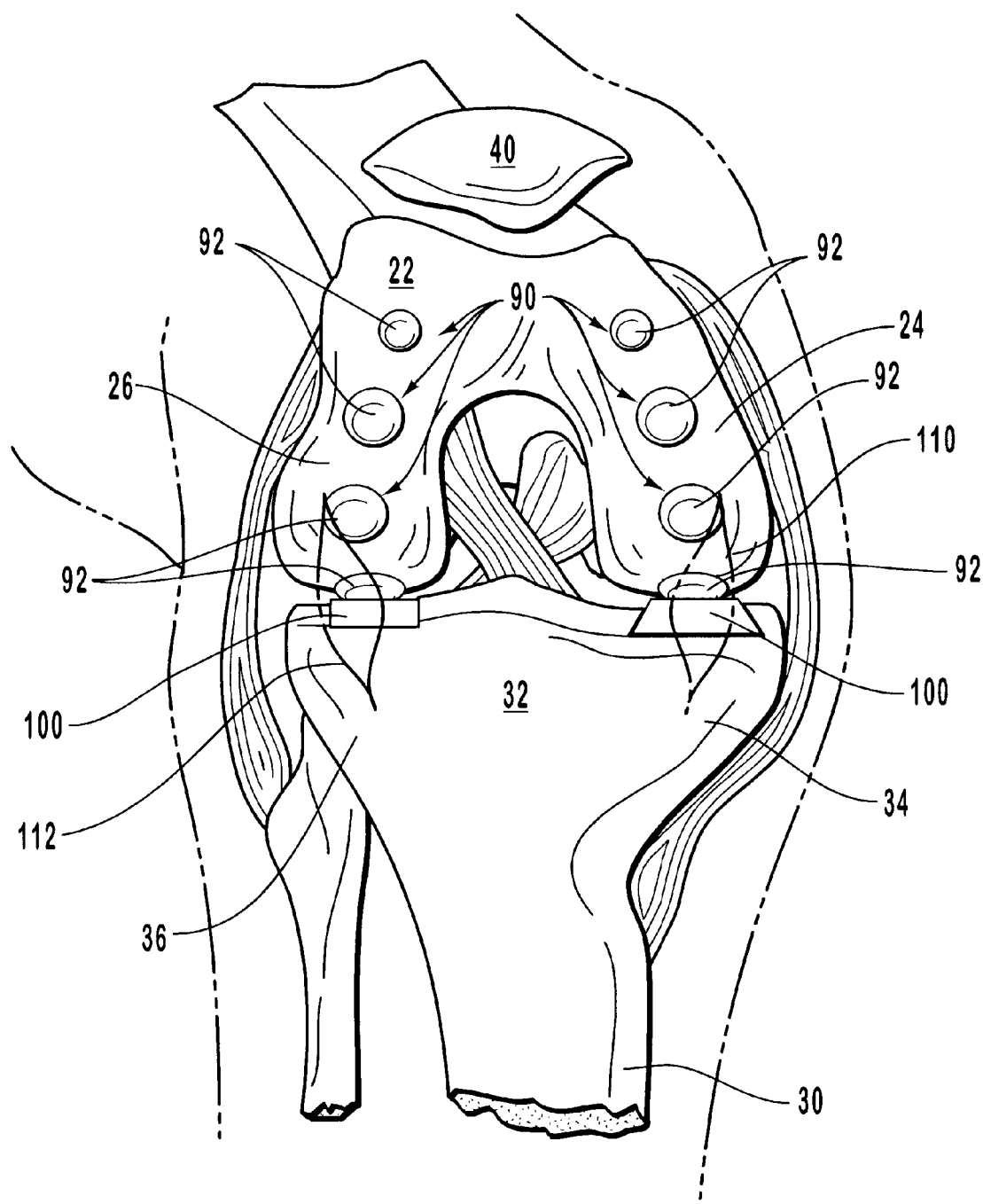
FIG. 10 is a partial cut-away perspective view of a knee joint that includes an alternate form of a tibial prosthetic component.

Generally, a single tibial component 100 is located within a channel 130 either adjacent to, near, or within each of medial plateau 34 and/or lateral plateau 36 of the proximal tibia 32 (as shown in FIGS. 8B, 8C, and 8D). It should be appreciated, however, that two or more tibial components 100 can be used, such as shown in FIGS. 9 and 10. In another configuration, only one tibial component 100 is required in either medial plateau 34 or lateral plateau 36.

Tibial component 100 can have various other configurations, shapes, and dimensions, such as those shown in FIGS. 7A–7C, which shall be described hereinafter. The various configurations can be chosen in light of the size of knee 10, the amount of damage to knee 10, the cooperation between tibial component 100 and femoral component 90, or other reasons that will be appreciated by one skilled in the art, such as but not limited to ligament tensioning.

Additionally, tibial component 100 may be fabricated from various materials such as metals, ceramics, plastics, or combinations thereof with or without porous ingrowth coatings. It is preferred that tibial component 100 be substantially composed of a metallic material.

Figure 6A:
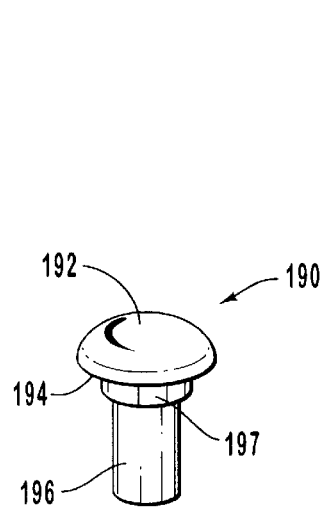
FIGS. 6A–6G are perspective views of alternate configurations of femoral components in accordance with the present invention.

FIG. 6A depicts, an alternate configuration of femoral component 190. The majority of the features previously discussed with respect to femoral component 90 also apply to femoral component 190. Femoral component 190 includes a transition portion 197 that extends from superior surface 194. Transition portion 197 includes sides that are substantially perpendicular to superior surface 194. The transition portion 197 of femoral component 190, in this configuration, can be countersunk into hole 82 formed in femur 20. By so doing, increased strength is give to the bond between femoral component 190 and femur 20 due to the increase in area in contact with the bone. It can be appreciated that the sides of femoral component 190 need not be substantially perpendicular to superior surface 194, but can be angularly oriented relative to superior surface 194.

Figure 6B:
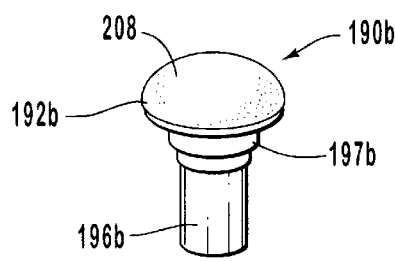

FIG. 6B depicts another alternate configuration of femoral component 190b. The majority of the features previously discussed with respect to femoral component 190 also apply to femoral component 190b. Femoral component 190b includes a multi-transition portion 197b that has a "step" configuration, such that the configuration of femoral component 190b allows countersinking of transition portion 197b of femoral component 190b in femur 20. Through the "step" configuration, femoral component 190b bonds more securely to femur 20. It can be appreciated that transition portion 197b may be repeated a number of times to increase the bonding. Additionally, femoral component 190b includes a coating 208 applied to lower surface 192b that reduces friction and allows smoother movement between the femoral and tibial components. Coating 208 may include a diamond coating, or any other coating that may reduce friction between the femoral and tibial components. Though it is preferred that femoral component 190b does not include coating 208, due to the difficult in preventing dislodging of coating 208 during use, it is contemplated that the present invention may use coating 208 if and when required.

Figure 6C:
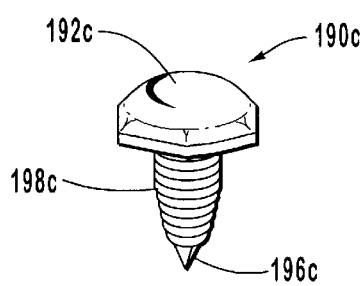

FIG. 6C depicts another alternate configuration of a femoral component 190c. The majority of the features previously disclosed with respect to femoral component 90 also apply to femoral component 190c. Stem 196c of femoral component 190c includes a plurality of raised portions 198c that project from the surface thereof. The particular configuration of the plurality of raised portions 198c may vary to assist in securely retaining femoral component 190c on femoral condyle 22. Therefore, the size, shape and configuration of the plurality of raised portions 198c may vary, so long as they cooperate with the size, shape and configuration of stem 196c to fixably attach femoral component 190c to femur 20. Therefore, raised portions 198c can take the form of angled wedges, threads, spikes, channels, or some other form to aid in locking stem 196c within femur 20.

The plurality of raised portions 198c on stem 196c is one structure capable of performing the function of attachment means for assisting in the attachment of femoral component 90 to femur 20. Other suitable structures are appropriate, and are known by one skilled in the art.

Figure 6D:
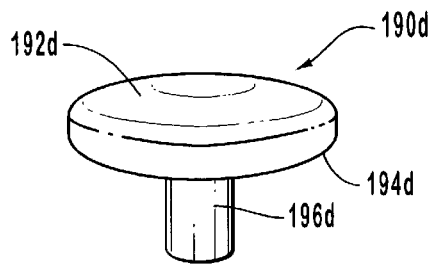

FIG. 6D depicts, another alternate configuration of a femoral component 190d. The majority of the features previously discussed with respect to femoral component 90 also apply to femoral component 190d. Femoral component 190d includes a spheroidal lower surface portion 192d that has a large cross-sectional area. The large surface area of lower surface portion 192d allows fewer femoral components 190d to be used during total or subtotal knee replacement; therefore, resulting in fewer holes 82 being formed in femur 20. By so doing, total or subtotal knee replacement is quicker and less invasive. Additionally, extending from and formed with lower surface portion 192d is a transition portion 197d that has the same cross-sectional dimension as the largest cross-sectional dimension of lower surface portion 192d. As previously discussed, transition portion 192d allows for a more secure attachment of femoral component 190d to femur 20 due to the increase surface area that comes into contact with femur 20.

Figure 6E:
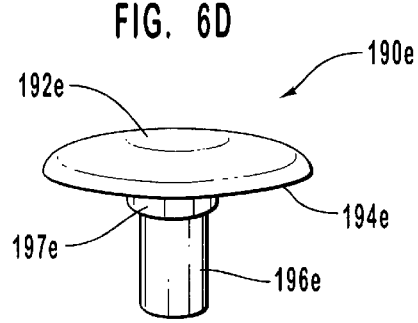

FIG. 6E depicts, another alternate configuration of a femoral component 190e. The majority of the features previously discussed with respect to femoral component 90 also apply to femoral component 190e. Femoral component 190e includes a transition portion 197e that extends from superior surface 194e. Transition portion 197e includes sides that are substantially perpendicular to superior surface 194e. Transition portion 197e of femoral component 190e, in this configuration, can be countersunk into hole 82 formed in femur 20. By so doing, increased strength is give to the bond between femoral component 190e and femur 20 due to the increase in area in contact with the bone. It can be appreciated that the sides need not be substantially perpendicular to superior surface 194e, but can be angularly oriented relative to superior surface 194e.

Figure 6F:
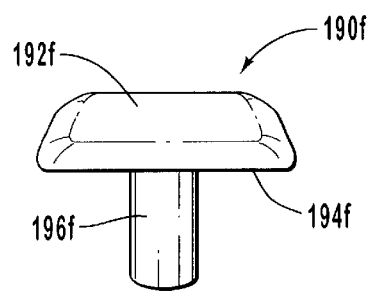

FIG. 6F depicts, another alternate configuration of a femoral component 190f. The majority of the features previously discussed with respect to femoral component 90 also apply to femoral component 190f. Femoral component 190f includes a spheroidal lower portion 192f that has a generally rectangular configuration. Lower portion 192f has a large cross-sectional area similar to that of lower portion 192e. The rectangular configuration allows a secure cooperation between lower portion 192f and a rectangular upper surface 102 of tibial component 100. The configuration of femoral component 190f further allows a surgeon to implant fewer femoral components 190f due to the larger surface area covered by each femoral component 190f.

Figure 6G:
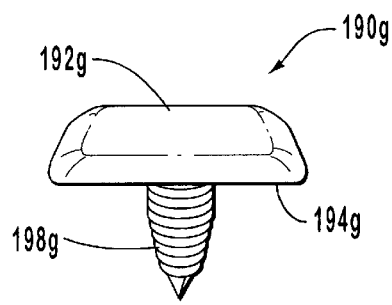

FIG. 6G depicts, another alternate configuration of a femoral component 190g. The majority of the features previously disclosed with respect to femoral component 90 also apply to femoral component 190g. Femoral component 190g has a similar form to that of femoral component 190f, however, stem 196g of femoral component 190g includes a plurality of raised portions 198g that project from the surface thereof. The particular configuration of plurality of raised portions 198g may vary to assist in securely retaining femoral component 190g on femoral condyle 22, as was described with reference to raised portions 198c.

The plurality of raised portions 198g on stem 196g is another structure capable of performing the function of attachment means for assisting in the attachment of femoral component 90 to femur 20. Other suitable structures are appropriate, and known by one skilled in the art.

Modification of the various configurations, dimensions, shapes, sizes and characteristics of femoral components 90, 190 and 190b–190g is possible, and include, but are not limited to, head diameters, stem diameters, inclusion or exclusion of threads, barbs or the like that act as attachment means, first and second transition portion diameters, depth parameters, surface finishes, and the like. Additionally, the configuration of femoral components 90, 190, and 190b–190g is such that it is possible to implant one or more femoral components 90, 190, and 190b–190g without the need to cut or sever any of the cruciate ligaments. As used herein the word "sever" will mean cutting, cleaving, detaching, separating, disconnecting, or otherwise stopping coupling of femur 20 and tibia 30 through the cruciate ligaments. It will be appreciated that the configurations of femoral components discussed herein are only illustrative and should not be considered as limiting the applicability of other femoral component configurations.

FIG. 7A depicts another alternative configuration of a tibial component 100a. The majority of features previously discussed with respect to the component 100, also apply to tibial component 100a. As shown, tibial component 100a includes a generally curved upper surface 102a. The particular configuration of upper surface 102a is such that increased matting is generated between femoral components 90, 190 and 190b–190g, and tibial components. As discussed previously, it can be appreciated that upper surface 102a may take various forms.

FIG. 7B depicts another alternate configuration of a tibial component 100b. The majority of the features previously disclosed with respect to tibial component 100 also apply to tibial component 100b. As shown, tibial component 100b includes at least one stem 106 extending from lower surface 104b that are capable of being fixably attached within one or more holes (not shown) formed in tibial plateau 32. Stems 106 can have various forms such as those described with reference to stems 96 and 196a–196g.

Tibial component 100b optionally includes a coating 108 formed on upper surface 102. Coating 108 is generally formed to aid in the reduction of frictional forces between femoral condyle 22 and tibial plateau 32. Such coating 108 may have a similar configuration as that of coating 208. Though it is preferred that upper surface 102b be polished or otherwise finished to reduce frictional forces, it is possible to use a coating 108 to perform the same function.

FIG. 7C depicts another alternate configuration of a tibial component 100c. The majority of the features previously disclosed with respect to tibial component 100 also apply to tibial component 100c. Tibial component 100c has a generally trapezoidal cross-section having an upper surface 102c and a lower surface 104c. The surface area of upper surface 102c is substantially smaller than lower surface 104c and has a smaller width. As such, when tibial component 100c is fixed within channel 130 that has a similar generally trapezoidal cross-section, as shown in FIG. 10, the combination of the configuration of tibial component 100c and channel 130 prevents movement of tibial component 100c generally parallel to the longitudinal axis of tibia 30. Through this configuration, tibial component 100c is more securely fixed within tibial plateau 32. It can be appreciated by one skilled in art that various other configurations of tibial component 100c are capable of performing a similar function.

Generally, tibial components 100, 100b, and 100c may have various sizes, dimensions, and shapes so long as tibial components 100, 100b, and 100c are capable of being implanted within tibia 30 without severing a cruciate ligament.

(d) Description of the Procedures and Protocols of the Presently Preferred Embodiments of the Present Invention The present invention will have application in reducing pain due to several knee disorders, and is particularly applicable for use in cases involving osteoarthritis, rheumatoid arthritis, and traumatic arthritis of the knee.

A candidate for implementation of the present invention is preferably chosen by considering several factors. Generally, a patient seeking the advice of an orthopedic surgeon complains of knee pain and stiffness, swelling of the joint accompanying diminished function. An examination of such a patient may reveal a limp, some discrepancy in the individual's limb length, or even severe misalignment of the limb. A radiological examination will often verify diagnosis of osteoarthritis, rheumatoid arthritis, and traumatic arthritis of the knee. Depending upon the classification of the condition and the particular suitability of the patient for the procedure, the patient will either be accepted or rejected as a candidate for the present invention.

During the procedure of the present invention, large portions of the patient's femoral and tibial condylar surfaces are saved. The configuration, size, shape, number, and position of the prosthetic components, of the present invention must be selected to properly complement the shape of the patient's medial and/or lateral plateau surfaces. Thus, it is helpful to utilize radiological and other examination techniques to carefully determine the size, shape, number, and position of femoral component 90 and tibial component 100 that would be best suited for a particular patient. It is anticipated that availability of a series of various sized and shaped prosthetic components will allow the surgeon to select a set that will provide an appropriate fit for a particular patient.

The presently preferred method of the present invention involves preparing the patient pre-operatively in a conventional fashion similar to that generally used for major knee surgery. Once the patient is taken to the operating room, the patient is preferably placed in a supine position and draping and preparation of the knee joint is completed. Anesthesia is also initiated.

While many surgical approaches to total knee replacement require a large incision, traversing from the lower portion of femur 20 or thigh over the patella of knee 10 and to the upper portion of the anterior tibia or leg, the present invention can be practiced using only small incisions or portals 110 and 112 (see FIG. 8A) on one or both sides of the patellar tendon (not shown), thereby minimizing the wound size and invasiveness of the surgical procedure. Furthermore, while present surgical procedures disrupt the quadricep mechanism: rectus femoris, vastus lateralis, vastus medialis, and vastus intermedius and the position of the patella or patellar ligaments, thereby increasing rehabilitation time, the use of small incisions 110 and 112 do not affect the quadricep mechanism or the position of the patella, again minimizing the wound size and invasiveness of the surgical procedure.

Small incisions 110 and 112 pass through the epidermis and dermis and are deepened through subcutaneous tissues and then the joint capsule, while hemostais is obtained by electrocautery. Each incision 110, 112 is so positioned as to allow access to femoral condyles 24, 26, and tibial plateaus 34 and 36, respectively, by way of open surgical procedures or through the use of arthroscopic procedures, as described in this illustrative embodiment of the method of the present invention. As such various types of equipment 120, both for arthroscopic and open surgical procedures, may be used and included, by way of example only, an arthroscope 122 and other types of surgical instruments 124, including saws, chisels, retractors, or suction apparatus.

The surgeon raises the patient's leg and bends knee 10 to allow examination of femoral condyles 22 and tibial plateaus 32 or "joint surfaces" to determine the best location for the components of the present invention. Specifically, the surgeon identifies the location of greatest wear on both femoral condyle 22 and tibial plateau 32. Additionally, the axis of knee 10 and rotational motion of knee 10 are analyzed to identify the desired implantation location. As part of knee axis and motion analysis, defects such as subchrondral lesions, are addressed before sizing of knee components to knee 10.

Utilizing FIGS. 8A–8D, reference will now be made to implantation of the various components of the present invention by way of an arthroscopic surgical procedure; however, it can be appreciated by one skilled in the art that implantation of the various components of the present invention may be performed through an open surgical procedure where no arthroscopic equipment us utilized. Discussion will further be made to implantation of components on medial condyles 24 and 34 of femur 20 and tibia 30, respectively. It can be appreciated, however, that a similar procedure may be performed through incision 112 with respect to lateral condyles 26 and 36 of femur 20 and tibia 30, if required.

A channel, generally indicated by reference numeral 130 in FIG. 8B, is formed in tibial plateau 32 and traverses medial plateau 34 of tibia 30. Channel 130 is formed to cooperate with femoral component 90 that is attached to medial plateau 34 of femur 20, thereby creating a separation of femur 20 and tibia 30. Channel 130 requires a portion of tibial surface 32 to be removed, preferably by using a reciprocating saw and chisel that pass through incision 110, that is maintained in the open position by way of retractors 126, as shown in FIG. 8A. Other methods are known by one skilled in the art to form channel 130 by way of open, "key-hole", and arthroscopic surgical techniques. As such, a saw is inserted through incision 110, while arthroscope 122 is inserted through incision 112 to allow light and observation of the surgical site. Alternatively, light and observation of the surgical site may be achievable by looking through incision 110, in the event that an open surgical procedure is performed. Whether through arthroscopic or open surgical procedures, portions of the proximal tibia 32 are removed until the required dimensions are achieved.

As shown, channel 130 has a generally rectangular cross-section, although other configurations are possible so long as channel 130 cooperates with tibial component 100.

Upon formation of channel 130, the position of knee 10 is manipulated as needed so as to allow access to femoral condyle 22 and associated surfaces of medial condyle 24. Once knee 10 is positioned, so as to render the desired portion of femoral condyle 22 visible to the surgeon, the surgeon verifies the axis of knee 10 and range of motion of knee 10 with respect to channel 130. After defining the axis of knee 10 and range of motion of knee 10 the surgeon defines the axis of medial condyle 24 of femur 20 and forms an anchoring hole 132, such as by way of a conventional arthroscopic surgical drill 125, as shown in FIG. 8B either alone or in combination with other surgical apparatus such as but not limited to one or more guide wires, jigs, and the like.

Anchoring hole 132 is sized and configured to cooperate with femoral component 90. However, anchoring hole 132 may be varied to accommodate femoral component 90 in its various forms, such as but not limited to those described herein. For example, anchoring hole 132 is countersunk to allow the required seating of superior surface 92 and transition portion 97 against various surfaces of medial condyle 24.

After channel 130 and anchoring hole 132 have been formed, the surfaces of femoral condyle 22 and tibial plateau 32 are thoroughly cleansed with a pulsating water lavage and antibiotic irrigation, while simultaneously, all waste products are removed from the surgical site via arthroscopic suction apparatus, as known by one skilled in the art. The selected femoral component 90 is inserted and secured within anchoring hole 132 by the use of PMMA, as shown in FIG. 8C. As can be appreciated, other methods, such as using porous bone ingrowth techniques, cements, or the like may be used to fix femoral component 90 in place. The combination of PMMA or other similar bonding techniques with raised portions 98 and stem 96 is another example of one structure capable of performing the function of attachment means for assisting in the attachment of femoral component 90 to femur 20.

Once femoral component 90 is inserted, the excess PMMA is removed from the surface of femoral condyle 22 such that no PMMA extends past femoral component 90. Femoral component 90 is inserted to a depth such that lower surface portion 92 of femoral component 90 protrudes from about 2 mm to about 15 mm above the femoral condyle surface 22. In an alternative configuration, femoral component 90 protrudes from about 4 mm to about 10 mm above the femoral condyle surface 22. In a preferred configuration, femoral component 90 protrudes about 5 mm to about 8 mm above the surface of femoral condyle surface 22.

Once femoral component 90 is in place, the surgeon manipulates knee 10 until the location for fixation of additional femoral components 90 is in sight through incision 110. Upon sighting of the next insertion site, the surgeon then follows the above procedure to implant another femoral component 90.

This process is repeated as necessary over as much of the surface of femoral condyle 22 as is necessary, including the intercondylar notch 28. Femoral condyle 22, therefore, may be covered with a plurality of femoral components 90, such as shown in FIGS. 8C, 8D, 9 and 10.

Upon completion of implantation of the desired number of femoral components 90, the surgeon next turns to the implantation of tibial component 100. Tibial component 100 is located within channel 130 and sized to effect a separation between femoral condyle 22 and tibial surface 32. Additionally, the configuration of tibial component 100 is such that the cooperation between femoral component 90 and tibial component 100 results in a stable joint.

Furthermore, the size and dimensions of tibial component 100 aid in the correction of malformations of femoral condyle 22 and/or tibial plateau 32 caused by the presence of subchrondral lesions. By so doing medial collateral ligaments 62, lateral collateral ligaments 64, anterior cruciate ligaments 66, and posterior cruciate ligaments are preserved, tightened, and maintain stability to knee 10.

Tibial component 100, as shown in FIG. 8C, is inserted into channel 130 and fixably attached by way of PMMA or some other method known by one skilled in the art or described herein. As described herein, tibial component 100 may have various configurations and dimensions to accommodate various knee problems. For example, multiple tibial components 100 can be used within each medial and lateral plateau 34 and 36 of tibia 30, as shown in FIGS. 9 and 10.

Once all requisite prosthetic components are in place to the satisfaction of the surgeon, as shown in FIG. 8C, 8D, 9 or 10, antibiotic irrigation is once again performed so as to reduce the possibility of infection, and equipment 120, whether arthroscopic procedure or open surgical procedure equipment is removed. Finally, the requisite surgical closing procedures are performed, such as insertion of a drain brought down anteriorly from the depths of the wound, and closure and dressing of the surgical wound. Once the surgical procedure is completed, the patient is taken to recover post-operatively, and X-rays may be obtained to check the results of the procedure.

As described herein, the insertion and fixation of tibial component 100 was described as occurring after the insertion and fixation of one or more femoral components 90. As will be appreciated by one skilled in the art, insertion and fixation of tibial component 100 may occur before insertion and fixation of femoral component 90. Additionally, insertion and fixation of tibial component 100 may occur before drilling of anchoring hole 132.

Generally speaking, the beneficial effects of the surgical procedure of the present invention assists in the substantial elimination of pain resulting from deterioration of the knee joint, in a substantially less evasive manner than presently taught, while providing strong and durable prosthesis. As such, the use of minor incisions, arthroscopic equipment, and lack of disruption to the surrounding muscles, tendons and ligaments results in a reduction in the risk of infection, an increase in the mobility and stability of the knee joint after surgery, and an accelerated hospital stay with less rehabilitation time.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A prosthetic knee component adapted for attachment to a surface of a patient's knee through a portal associated with a minimally invasive surgical procedure, the prosthetic knee component comprising:

a first portion sized and shaped so as to be adapted for fixable attachment to the surface of the knee through a portal associated with a minimally invasive surgical procedure while substantially maintaining the existing shape of one or more condyles of the femur; and an elongated, generally spheroidal second portion disposed opposite to said first portion, said second portion being sized and shaped so as to be adapted to extend over a portion of the surface of the knee between an anterior portion and a posterior portion of the knee through a portal associated with a minimally invasive surgical procedure.

2. The prosthesis as recited in claim 1, wherein said second portion extends between the anterior portion and the posterior portion of a femur.

3. The prosthesis as recited in claim 1, wherein said second portion is adapted to reduce friction.

4. The prosthesis as recited in claim 1, wherein said first portion includes attachment means for assisting the attachment of the prosthetic component to the surface of the knee.

5. The prosthesis as recited in claim 4, wherein said attachment means comprises a plurality of raised portions extending from said first portion.

6. The prosthesis as recited in claim 1, wherein said second portion has a generally oval configuration.

7. The prosthesis as recited in claim 1, wherein the prosthetic knee component further includes a transition portion intermediate of said first portion and said second portion.

8. The prosthesis as recited in claim 1, wherein said first portion is adapted with at least one thread that substantially encompasses said first portion.

9. A knee joint prosthesis for attachment to a femur and a tibia of a patient during unicompartmental or total knee replacement, the prosthesis comprising:

a plurality of femoral components configured to be attached to the femur, each of said plurality of femoral components having a first portion adapted for fixable attachment to the femur and an elongated second portion formed with a spheroidal bearing surface and adapted to extend over a portion of the femur between an anterior portion and a posterior portion of the femur, said femoral component being configured so as to permit attachment to the femur through one or more portals associated with a minimally invasive surgical procedure while substantially maintaining the existing shape of one or more condyles of the femur and without severing both of the cruciate ligaments; and at least one tibial component having a first surface adapted to cooperate with the tibia and a second surface adapted to cooperate with at least two of said plurality of femoral components affixed to the femur disposed opposite the at least one tibial component affixed to the tibia, said tibial component being configured so as to permit attachment to said tibia through one or more portals associated with a minimally invasive surgical procedure and without severing both of the cruciate ligaments.

10. The prosthesis as recited in claim 9, wherein said first portion of said femoral component includes a stem for insertion into said femur.

11. The prosthesis as recited in claim 9, wherein said tibial component has a generally rectangular form, wherein said first surface and said second surface are substantially planar.

12. The prosthesis as recited in claim 9, wherein said tibial component is formed from two tibial component portions.

13. The prosthesis as recited in claim 9, wherein said bearing surface is covered with a friction reducing coating.

14. The prosthesis as recited in claim 9, wherein said femoral component further comprises a transition portion intermediate of said first portion and said second portion.

15. The prosthesis as recited in claim 9, wherein said second portion has an oval configuration.

16. A total knee joint prosthesis, comprising:

a femoral component sized and shaped so as to be adapted for attachment to a femur of a patient through a portal associated with a minimally invasive surgical procedure while substantially maintaining the existing shape of one or more condyles of the femur, said femoral component comprising an elongated, spheroidal portion and a stem extending from said elongated, spheroidal portion; and a tibial component having a first surface configured to aid in attachment of said tibial component to a tibia and a second surface adapted to cooperate with said elongated, spheroidal portion of said femoral component.

17. The prosthesis as recited in claim 16 wherein said stem is formed with attachment means for assisting the attachment of said femoral component to said femur.

18. The prosthesis as recited in claim 17, wherein said attachment means includes a plurality of raised portions.

19. The prosthesis as recited in claim 16, wherein said first surface includes a stem extending therefrom.

20. The prosthesis as recited in claim 16, wherein said tibial component has a generally trapezoidal configuration with said second surface having a curved profile to cooperate with said elongated, spheriodal portion.

21. The prosthesis as recited in claim 16, wherein said second surface is angularly orientated relative to said first surface.

22. A method of repairing a patient's damaged knee, while preserving at least one cruciate ligament, comprising the steps of:

obtaining a prosthetic component sized an shaped so as to be adapted for fixable attachment to a surface of the patient's knee through a portal associated with a minimally invasive surgical procedure and being capable of separating a femoral condyle and a tibial plateau, the prosthetic component comprising:

a first portion adapted for fixable attachment to the femoral condyle of the knee; and an elongated, generally spheriodal second portion disposed opposite said first portion, said second portion being adapted to cover a portion of the surface of the knee between an anterior portion and a posterior portion of the surface of the knee;

preparing the patient's knee for implantation of said prosthetic component by way of at least two minimally invasive portals formed in tissues surrounding the femoral condyle and the tibial plateau, the at least two small portals so configured to result in minor wounds following repairing the patient's damaged knee; and implanting said prosthetic component into the surface of the knee by way of said at least two portals thereby separating portions of the femoral condyle and the tibial plateau.

23. The method as recited in claim 22, wherein said knee joint prosthesis further comprises a tibial component having an upper surface adapted to cooperate with said second portion.

24. The method as recited in claim 23, wherein said tibial component comprises a first surface adapted to cooperate with the tibial plateau and a second surface adapted to cooperate with said second portion.

25. The method as recited in claim 22, wherein the step of preparing the patient's knee comprises:

creating at least two portals in the knee to allow access to the knee joint; and positioning at least one surgical apparatus through at least one of said at least two portals.

26. The method as recited in claim 22, wherein the step of implantation comprises:

identifying the motion of the knee joint;

verifying the implantation location of the knee joint prosthesis based on the motion of the knee joint;

forming one or more anchoring holes to accommodate the knee joint prosthesis; and fixing the knee joint prosthesis within the knee joint by way of the anchoring hole.

27. The method as recited in claim 26, wherein the step of forming one or more anchoring holes comprises drilling one or more anchoring holes in the femoral condyle.

28. The method as recited in claim 27, further including the step of forming a channel in a tibial plateau, the channel being adapted to receive a tibial component.

29. The method as recited in claim 28, wherein the fixing step comprises positioning the first portion within one of said one or more anchoring holes and fixing in place through attachment means for assisting in attachment of the first portion to the femoral condyle.

30. The method as recited in claim 29, wherein the attachment means comprises a combination of a plurality of raised portions with a material selected from the group consisting of cements, porous bone ingrowth techniques, and polymethyl methacrylate.

31. The method as recited in claim 29, wherein the attachment means comprises polymethyl methacrylate.

32. A method of repairing a patient's damaged knee, comprising the steps of:

obtaining a component comprising a first portion sized and shaped so as to be adapted for fixable attachment to a surface a patient's knee through a portal associated with a minimally invasive surgical procedure, and a second portion sized and shaped so as to be introduced through a portal associated with a minimally invasive surgical procedure, said second portion including an elongated bearing surface adapted to cover a portion of the surface of the patient's knee between an anterior portion and a posterior portion of the surface of the patient's knee;

removing a portion of the patient's knee through one or more portals to create one or more anchoring holes while preserving substantially all other portions of the patient's knee and both cruciate ligaments; and fixing said component within one of said one or more anchoring holes such that a portion of said bearing surface extends above said distal end of the surface of the patient knee.

33. The method as recited in claim 32, further comprising:

obtaining a tibial component having a first surface adapted to cooperate with a surface of a tibia and a second surface adapted to cooperate with said bearing surface of said femoral component;

removing a portion of said tibia to create a channel to receive said tibial component; and fixing said tibial component within said channel such that said second surface cooperates with said bearing surface to substantially separate said distal end of said femur from said tibia.

34. The method as recited in claim 32, further comprising the step of creating one or more portals that are minimally invasive to the patient.

35. The method as recited in claim 32 wherein the step of removing a portion of the patient's knee comprises drilling said anchoring holes in said patient's femur with a surgical drill through at least one of said one or more portals.

36. The method as recited in claim 35, wherein the step of fixing femoral component comprises cementing said first portion of said femoral component into one of said one or more anchoring holes.

37. The method as recited in claim 36, wherein the step for fixing femoral component comprises a step for attaching said first portion by way of polymethyl methacrylate.

38. The method as recited in claim 33, wherein the step of removing a portion of said tibia comprises sawing and chiseling a portion of said patient's tibia through one or more portals created in the patient's knee.

39. The method as recited in claim 38, wherein the step of fixing said tibial component comprises attaching said first surface to said tibia by way of polymethyl methacrylate.

* * * * *